US005800819A

United States Patent [19]
Wambebe et al.

[11] Patent Number: 5,800,819
[45] Date of Patent: Sep. 1, 1998

[54] PIPER GUINEENSE, PTEROCARPUS OSUN, EUGENIA CARYOPHYLLATA, AND SORGHUM BICOLOR EXTRACTS FOR TREATING SICKLE CELL DISEASE

[75] Inventors: Charles Wambebe, Abuja; P. O. Ogunyale, Oyo; K. S. Gamaniel, Abuja; R. N. Nasipuri, Abuja; J. I. Okogun, Abuja; Babatunde Samuel, Abuja; Akin Olusola, Abuja; Abayomi Orisadipe, Abuja, all of Nigeria

[73] Assignee: National Institute for Pharmaceutical Research and Development Federal Ministry of Science and Technology, Abuja, Nigeria

[21] Appl. No.: 786,313

[22] Filed: Jan. 21, 1997

[30] Foreign Application Priority Data

Jan. 25, 1996 [NG] Nigeria .................................. RP.12369

[51] Int. Cl.$^6$ ........................................................ A61K 35/78
[52] U.S. Cl. .......................... 424/195.1; 514/814; 514/815
[58] Field of Search ........................ 424/195.1; 514/814, 514/815

[56] References Cited

U.S. PATENT DOCUMENTS

| 4,473,559 | 9/1984 | Robinson | 424/195.1 |
| 5,225,447 | 7/1993 | Weinheimer | 514/549 |
| 5,447,720 | 9/1995 | Fadulu | 424/195.1 |
| 5,449,516 | 9/1995 | De Araujo | 424/195.1 |

OTHER PUBLICATIONS

Houston, Amer. J. Clin. Nutr., 26:1261–1264, 1973.

*Primary Examiner*—David M. Naff
*Assistant Examiner*—Janet M. Kerr
*Attorney, Agent, or Firm*—Shook, Hardy & Bacon L.L.P.

[57] ABSTRACT

A phytochemical composition for treating sickle cell disease is provided. The composition is a cold water extraction product of a mixture containing *Piper guineenses* seeds, *Pterocarpus osum* stem, *Eugenia caryophyllum* fruit, *Sorghum bicolor* leaves and potash. Also described are mixtures of phytomaterials used for preparing the extraction product, methods for making the extraction product, and methods for using the extraction product.

13 Claims, No Drawings

*PIPER GUINEENSE, PTEROCARPUS OSUN, EUGENIA CARYOPHYLLATA,* AND *SORGHUM BICOLOR* EXTRACTS FOR TREATING SICKLE CELL DISEASE

BACKGROUND OF THE INVENTION

1. Field of the Invention

The present invention relates to the field of phytodrugs, and in particular the invention relates to phytodrugs for treatment and management of sickle cell disease and methods of preparing and using same.

2. Prior Activities and Problems in the Field

Sickle Cell Disease (SCD) is a genetic disorder which, in particular, shows its clinical manifestations in the Black race. At the present time there is no known safe drug for the management of this disease anywhere in the world. Nigeria, being the most populous Black nation in the world, has the highest incidence of SCD. Conservatively it is estimated that over 2 million Nigerians suffer from SCD while another 25 million Nigerians are carriers. About 100,000 babies are born every year with SCD and it causes approximately 8% of all infant deaths each year.

The morbidity and mortality factors associated with sickle cell disease are well-known. The acute and chronic trauma of the painful crisis are beyond description. In view of these realities, there is a constant need for drugs which might alleviate the effects of this terrible disease. And the search for such drugs is of the highest priority.

The first known case of SCD involving a 20 year old West Indian student studying in America was described by Herrick in 1910. However, centuries before Herrick documented this case, SCD was known to the people of West Africa. In fact, archaeological research in Nigeria has unearthed 700-year-old human bones showing evidence of sickle cell infarcts.

SCD is a hereditary disease of the red blood cells characterized by the presence of an abnormal gene that causes production of abnormal hemoglobin of the sickle or "S" variety. It is not known exactly when, how, or where the mutation producing the sickle cell gene occurs, but the sickle cell gene is found to be prevalent in malaria endemic regions of tropical Africa.

The relationship of the sickle cell gene to *P. falciparum* malaria has become a classic example of natural selection in man. The high mortality of children in endemic countries due to malaria makes it a powerful selective influence for factors that confer resistance. It is generally accepted that the hemoglobin AS system represents a balanced polymorphism in nature and that the force sustaining the high frequency of HbS is endemic malaria, especially *P. falciparum* malaria. It is thought that human populations in such high malaria endemic areas evolved high frequency of genes that in the heterozygotes hardly causes genetic disease per se and leaves a selective advantage to the populations concerned, i.e., that the heterozygote sickle state (AS) confers a survival advantage over the normal AA individual. It is postulated that the "S" gene accords a relative protective effect against severe forms of *P. falciparum* malaria such that a child with the sickle cell trait (AS) has a better chance of survival to adult age than the non-sickler. However, the exact mechanism(s) through which HbS protects against severe malaria still remains unclear.

Accelerated sickling and preferential destruction of parasitized red blood cells as compared to non-parasitized red blood cells, especially in a hypoxic micro-environment, has been postulated. Also, the HbS polymer may inhibit parasite growth or interfere with some other critical functions of the parasite. It must be emphasized that these postulates do not suggest that sickle cell trait individuals are resistant to infection by *P. falciparum*, but rather that they are less likely to die of the infection than individuals with normal Hb. On the other hand, in the sickle cell patient, acute malaria constitutes a life threatening event by means of its propensity for initiating vaso-occulisive and anaemic crises.

The acute complications that have constituted major causes of mortality in SCD include the following:

(a) Overwhelming bacterial infection (meningitis and septicaemia from *Strep. pneumonia* or *H. influenzae* infection), and in this regard, the combination of penicillin prophylaxis and multi-valent pneumococcal vaccination have been shown to decrease incidence and mortality in the United States and is currently being introduced to some West African Countries;

(b) Acute chest syndrome;

(c) Acute splenic sequestration;

(d) Cerebro-vascular accident (C.VA); and (e) Aplastic crisis.

However, painful episodes are by far the most common complications of SCD. About 70% of patients with painful episodes do not even seek professional medical assistance. But one of the primary goals of management of painful episodes is to alleviate pain and suffering. And since painful episodes are never life threatening, it is important also to reduce the level of anxiety in the patient and family. Placebos have no place in the management of pain.

SUMMARY OF THE INVENTION

It is a primary objective of the present invention to provide a phytodrug that is useful in the care and management of sickle cell disease in persons afflicted with such disease. It is also an objective of the invention to provide methods for preparing a useful phytodrug and for treating persons afflicted with sickle cell disease.

With the foregoing in mind, the present invention provides a composition for treating sickle cell disease comprising a cold water extraction product of a mixture containing *Piper guineenses* seeds, *Pterocarpus osum* stem, *Eugenia caryophyllum* fruit, and *Sorghum bicolor* (caudatum) leaves. The mixture may also include potash. In a preferred form of the invention the mixture may include from about 12 to about 17 parts by weight of said *Piper guineenses* seeds, from about 15 to about 19 parts by weight of said *Pterocarpus osum* stem, from about 12 to about 18 parts by weight of said *Eugenia caryophyllum* fruit, from about 25 to about 32 parts by weight of said *Sorghum bicolor* leaves and from about 15 to about 22 parts by weight of said potash. In its presently most preferred form, the mixture may include about 15.8 percent by weight of said *Piper guineenses* seeds, about 18.4 percent by weight of said *Pterocarpus osum* stem, about 13.2 percent by weight of said *Eugenia caryophyllum* fruit, about 31.6 percent by weight of said *Sorghum bicolor* leaves, and about 21.0 percent by weight of said potash.

The invention also provides a composition for preparing a drug effective for treating sickle cell disease which comprises a mixture containing *Piper guineenses* seeds, *Pterocarpus osum* stem, *Eugenia caryophyllum* fruit, and *Sorghum bicolor* leaves. The mixture may also include potash.

In another aspect the invention provides a method for preparing a composition for treating sickle cell disease. The

3 method includes the steps of forming a mixture containing *Piper guineenses* seeds, *Pterocarpus osum* stem, *Eugenia caryophyllum* fruit, and *Sorghum bicolor* leaves and subjecting said mixture to extraction using cold water to thereby form an extract containing a drug material effective for treating said sickle cell disease. The mixture may also include potash.

The invention also provides a method for treating a human afflicted with sickle cell disease. In this aspect of the invention the method includes forming a mixture containing *Piper guineenses* seeds, *Pterocarpus osum* stem, *Eugenia caryophyllum* fruit, and *Sorghum bicolor* leaves, subjecting said mixture to extraction using cold water to thereby form an extract containing a drug material effective for treating said sickle cell disease, and treating a human afflicted with sickle cell disease with said drug material. In this aspect of the invention also the mixture may include potash. In accordance with the invention, a dose of approximately 166.7 mg of said drug material may be administered orally to a person afflicted with sickle cell disease.

DETAILED DESCRIPTION OF PREFERRED EMBODIMENTS OF THE INVENTION

In accordance with the invention, a composition for treating sickle cell disease is provided. The composition consists of a cold water extraction product of a mixture containing *Piper guineenses* seeds, *Pterocarpus osum* stem, *Eugenia caryophyllum* fruit, and *Sorghum bicolor* leaves. Preferably the initial mixture may also include potash. Generally the initial mixture from which the extraction product is prepared will include from about 12 to about 17 parts by weight of *Piper guineenses* seeds, from about 15 to about 19 parts by weight of *Pterocarpus osum* stem, from about 12 to about 18 parts by weight of *Eugenia caryophyllum* fruit, from about 25 to about 32 parts by weight of *Sorghum bicolor* leaves, and from about 15 to about 22 parts by weight of said potash.

Phytochemical screening indicates that the extraction product contains flavonoids, alkaloids, saponins, tannins, glycosides and traces of anthraquinones. However, the extraction product does not include steroids or fatty acids. In this regard it is postulated that the major contributor to the anti-sickling properties of the drug materials of the invention may be the tannin content of the *Eugenia caryophyllum* fruit. Moreover, it is believed also that the other ingredients of the extracted drug materials may have a synergistic effect which enhances the beneficial effect of the drug materials overall when used in connection with the treatment and management of sickle cell disease.

In accordance with the preferred form of the invention, the initial mixture from which the extraction product is prepared includes about 15.8 percent by weight of *Piper guineenses* seeds, about 18.4 percent by weight of *Pterocarpus osum* stem, about 13.2 percent by weight of *Eugenia caryophyllum* fruit, about 31.6 percent by weight of *Sorghum bicolor* leaves, and about 21.0 percent by weight of potash.

The various raw materials described above are weighed, mixed together and then subjected to cold water extraction for 24 hrs. The fluid containing the extract is then decanted and filtered and the residue is discarded. The filtrate is freeze-dried for 48 hours using a Finn-Aqua Lyovac GT3 freeze dryer to provide a dry powder containing the active drug materials extracted from the initial mixture.

The powder containing the active drug materials may then be formulated into capsule dosage form. Each capsule may preferably contain 166.7 mg of the freeze-dried powder and inert additives in sufficient quantities to provide a 300 mg per capsule.

It has been determined that the most effective daily dosage consists of four capsules for adults and two capsules for children. The daily dosages should be administered in two divided doses with one-half of the daily dosage taken twice daily. Preferably the separate divided doses will be taken in the morning and again in the evening.

In accordance with the invention, it was initially observed that the extracted drug materials described above protected red blood cells obtained from sickle cell patients against sickling when such cells were exposed to low oxygen tension. This effect lasted for over 48 hours while the protection was about 91%. Furthermore, laboratory data clearly indicated the dose dependant reversal of already sickled red blood cells using the described plant extracts. This reversal also lasted for over 48 hours and the effect was 100%. These tests indicated that the extract had scientific justification for possible beneficial effect in sickle cell patients. Safety evaluation tests were therefore conducted. The data obtained from such evaluation tests clearly show that the product is very safe. Carcinogenicity and mutagenicity evaluation was also conducted and the obtained results indicate that the described drug materials are devoid of such adverse effects.

The World Health Organization (WHO) has policies concerning the development of herbal medicine. WHO clearly advises that when a plant based product (e.g. herbal medicine) is safe and indicates efficacy, it can be subsequently standardized and formulated into suitable dosage form for clinical trials. In accordance with the present invention, the procedures and policies recommended by WHO have been followed in developing and testing the efficacy of the drug materials of the present invention. Thus, the drug materials of the invention were standardized and formulated into capsule dosage form as described above.

Clinical trial phase I was conducted using staff of the Nigerian National Institute for Pharmaceutical Research and Development (NIPRD) as volunteers. The clinical parameters of the blood chemistry, the liver functional status as well as kidney functional status were assessed. It was thus determined that the drug materials of the invention had no adverse effect on the volunteers regarding all the parameters studied.

Initially during the phase II clinical trials, the staff of NIPRD went regularly to the homes of patients so as to make vital observations with respect to the response of the patients to the new drug materials of the invention. Later, due to the encouraging results obtained, the visits were reduced to once a month. After one and one-half years, the patients were seen only about once every two months at clinics established by NIPRD. The clinical status of each patient was assessed by medical doctors at these clinics.

Laboratory tests were conducted to evaluate the functional status of the liver, the kidneys and the blood chemistry. Approximately 500 patients coming from different parts of Nigeria were involved in the testing. Because of the large number of patients involved, three clinics in all were established by NIPRD to attend to patients involved in the clinical trials.

From the data obtained it has been determined that the new drug materials of the invention have no detectable adverse affect on the kidney, liver and the blood chemistry. The values recorded for these parameters fall within normal range. On the average, about 90% of the patients involved in the clinical trials have not experienced any major sickle cell disease crisis since they entered the clinical trial program. Even the few patients (10%) who have experienced crises reported that such crises were less frequent and less severe as compared to their experiences before they joined the clinical trial program.

The patients involved in the clinical trial program had improved appetites accompanied by appreciable weight gain. There was less incidence of anaemia and jaundice, most likely due to the reduced rate of destruction of the red blood cells. It was also observed that with patients involved in the clinical trial program whose tests indicated 60–90% sickling with sodium metabisulphite at the beginning of the study, such sickling tendencies had completely disappeared after about 8 months of using the drug materials provided by the present invention. These results are clearly highly encouraging and probative of the efficacy of the drug materials of the invention.

We claim:

1. A composition for treating sickle cell disease comprising a cold water extraction product of a mixture containing from about 12 to about 17 parts by weight of *Piper guineense* seeds, from about 15 to about 19 parts by weight of *Pterocarpus osun* stem, from about 12 to about 18 parts by weight of *Eugenia caryophyllata* fruit, and from about 25 to about 32 parts by weight of *Sorghum bicolor* leaves.

2. A composition as set forth in claim 1, wherein said mixture comprises from about 15 to about 22 parts by weight of potash.

3. A composition as set forth in claim 2, wherein said mixture comprises about 15.8 percent by weight of said *Piper guineense* seeds, about 18.4 percent by weight of said *Pterocarpus osun* stem, about 13.2 percent by weight of said *Eugenia caryophyllata* fruit, about 31.6 percent by weight of said *Sorghum bicolor* leaves, and about 21.0 percent by weight of said potash.

4. A composition for preparing a drug effective for treating sickle cell disease comprising a mixture containing from about 12 to about 17 parts by weight of *Piper guineense* seeds, from about 15 to about 19 parts by weight of *Pterocarpus osun* stem, from about 12 parts to about 18 parts by weight of *Eugenia caryophyllata* fruit, and from about 25 to about 32 parts by weight of *Sorghum bicolor* leaves.

5. A composition as set forth in claim 4, wherein said mixture comprises from about 15 to about 22 parts by weight of potash.

6. A composition as set forth in claim 5, wherein said mixture comprises about 15.8 percent by weight of said *Piper guineenses* seeds, about 18.4 percent by weight of said *Pterocarpus osum* stem, about 13.2 percent by weight of said *Eugenia caryophyllum* fruit, about 31.6 percent by weight of said *Sorghum bicolor* leaves, and about 21.0 percent by weight of said potash.

7. A method for preparing a composition for treating sickle cell disease comprising:

forming a mixture containing from about 12 to about 17 parts by weight of *Piper guineense* seeds, from about 15 to about 19 parts by weight of *Pterocarpus osun* stem, from about 12 to about 18 parts by weight of *Eugenia caryophyllata* fruit, and from about 25 to about 32 parts by weight of *Sorghum bicolor* leaves; and subjecting said mixture to extraction using cold water to thereby form an extract containing a drug material effective for treating said sickle cell disease.

8. A method as set forth in claim 7, wherein said mixture comprises from about 15 to about 22 parts by weight of potash.

9. A method as set forth in claim 8, wherein said mixture comprises about 15.8 percent by weight of said *Piper guineense* seeds, about 18.4 percent by weight of said *Pterocarpus osun* stem, about 13.2 percent by weight of said *Eugenia caryophyllata* fruit, about 31.6 percent by weight of said *Sorghum bicolor* leaves, and about 21.0 percent by weight of said potash.

10. A method for treating a human afflicted with sickle cell disease comprising:

forming a mixture containing from about 12 to about 17 parts by weight of *Piper guineense* seeds, from about 15 to about 19 parts by weight of *Pterocarpus osun* stem, from about 12 to about 18 parts by weight of *Eugenia caryophyllata* fruit, and from about 25 to about 32 parts by weight of *Sorghum bicolor* leaves;

subjecting said mixture to extraction using cold water to thereby form an extract containing a drug material effective for treating said sickle cell disease; and treating a human afflicted with sickle cell disease with said drug material.

11. A method as set forth in claim 10 wherein said mixture comprises from about 15 to about 22 parts by weight of potash.

12. A method as set forth in claim 11, wherein said mixture comprises about 15.8 percent by weight of said *Piper guineenses* seeds, about 18.4 percent by weight of said *Pterocarpus osum* stem, about 13.2 percent by weight of said *Eugenia caryophyllum* fruit, about 31.6 percent by weight of said *Sorghum bicolor* leaves, and about 21.0 percent by weight of said potash.

13. A method as set forth in claim 12 where a dose of approximately 166.7 mg of said drug material is administered orally to said person afflicted with sickle cell disease.

* * * * *